United States Patent [19]
Satoh et al.

[11] Patent Number: 6,063,955
[45] Date of Patent: May 16, 2000

[54] METHOD FOR PRODUCING OPTICALLY ACTIVE ERYTHRO-3-AMINO-2-HYDROXYBUTYRIC ESTERS AND ACIDS THEREOF

[75] Inventors: Hisao Satoh; Kenichi Yamamoto, both of Saitama, Japan

[73] Assignee: Nippon Kayaku Kabushiki Kaisha, Tokyo, Japan

[21] Appl. No.: 09/230,908

[22] PCT Filed: Sep. 12, 1997

[86] PCT No.: PCT/JP97/03228

§ 371 Date: Feb. 3, 1999

§ 102(e) Date: Feb. 3, 1999

[87] PCT Pub. No.: WO97/03228

PCT Pub. Date: Mar. 19, 1998

[30] Foreign Application Priority Data

Sep. 13, 1996 [JP] Japan .................................. 8-263802

[51] Int. Cl.[7] ...................... C07C 229/16; C07C 229/12; C07C 229/14
[52] U.S. Cl. .............................. 560/29; 560/39; 560/160; 560/170; 562/444; 562/555; 562/567
[58] Field of Search ................................ 560/39, 170, 29, 560/160; 592/444, 555, 567

[56] References Cited

U.S. PATENT DOCUMENTS 5,523,463  6/1996  Hilpert ..................... 560/137

FOREIGN PATENT DOCUMENTS

| 0 827 943 | 3/1998 | European Pat. Off. . |
| 50-137911 | 11/1975 | Japan . |
| 5-1000 | 1/1993 | Japan . |
| 5-25107 | 2/1993 | Japan . |
| 7-165678 | 6/1995 | Japan . |

OTHER PUBLICATIONS

Organic Chemistry 4th ed. Pine, Hendrickson, Cram and Hammond, McGraw Hill 1980, p319, 1980.
'Diastereoselective catalytic asymmetric nitroaldol reaction utilizing rare earth–Li–(R)–BINOL complex. A highly effecient synthesis of Norstatine.' SASAI et al., Tetrahedron Letters, 1994, vol. 35, No. 33, p. 6123–6126, 1994.
J.Pract. Chem., 1973, vol. 315, No. 4, p.611–619 (cited in Search Report).
Copy of the International Search Report dated Dec. 9, 1997.
Journal f. prakt. Chemie, vol. 315, Issue 6, 1973, p. 1045–1056, J.A. Barth, Leipzig, together with the English translation.

*Primary Examiner*—Gary Geist
*Assistant Examiner*—Brian J. Davis
*Attorney, Agent, or Firm*—Nields, Lemack & Dingman

[57] ABSTRACT

A method for producing an optically active erythro-3-amino-2-hydroxybutyric ester as an important intermediate of pharmaceutical agents, specifically HIV protease inhibitor, in high purity and in high yield. The method includes producing an optically active erythro-3-amino-2-hydroxybutyric ester by oxidizing the hydroxyl group at the 2-position of an optically active 3-amino-2-hydroxybutyric ester, optically active at the 3-position, as represented by formula (I):

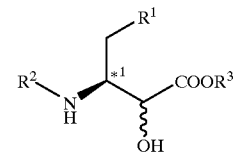

(I)

(wherein $R^1$ represents a phenyl group or a cyclohexyl group; $R^2$ represents a protective group and $R^3$ represents an unsubstituted or substituted alkyl residue; the steric configuration of *1 represents S configuration or R configuration), and then reducing erythro-selectively the resulting product by using aluminum alkoxide.

4 Claims, No Drawings

METHOD FOR PRODUCING OPTICALLY ACTIVE ERYTHRO-3-AMINO-2-HYDROXYBUTYRIC ESTERS AND ACIDS THEREOF

TECHNICAL FIELD

The present invention relates to a method for producing optically active erythro-3-amino-2-hydroxybutyric esters and acids thereof, for example, having (2S, 3S) configuration, as the important intermediates of pharmaceutical agents, for example HIV protease inhibitor.

BACKGROUND ART

Concerning methods for producing optically active 3-amino-2-hydroxybutyric esters, a great number of reports have been issued, including methods by cyanohydration of aldehyde, for example, as described in Bulletin of the Chemical Society of Japan, 65, 360 (1992), Tetrahedron Letters, 33 (45), 6763 (1992) or methods using diethyl malate as a starting material as described in Tetrahedron Letters, 33 (45), 6803 (1992), and methods using tartaric acid as a starting material as described in Chemical & Pharmaceutical Bulletin, 39 (10), 2550 (1991), but most of the methods are for the purpose of producing threo compounds. About methods for producing erythro compounds, reports have already been presented, including, for example, the method by asymmetric hydrogenation reaction using asymmetric catalysts (Japanese Patent Laid-open No.1000/1993), the method by the condensation of 2-hydroxy-3-nitropropanic derivatives with aldehyde (Japanese Patent Laid-open No.165678/1995), the method using cyanohydration which is erythro selectivity by the phthaloyl protection of amino group (Japanese Patent Laid-open No.309840/1995), the method by nitroaldol reaction using asymmetric catalysts (Tetrahedron Letters, 35 (33), 6123 (1994)).

According to the method disclosed in Japanese Patent Laid-open No.1000/1993 among the methods for producing the erythro compounds, asymmetry is introduced by hydrogenation reaction using asymmetric catalysts, so a high hydrogen pressure (100 atm) is required and four isomers are produced because the starting material is not an optically active substance. Taking account of the fact that chemically unstable azide compounds are intermediately produced for the introduction of amino group, the method encounters a great number of problems for the industrial application thereof. Additionally, the method disclosed in Japanese Patent Laid-open No.165678/1995 requires the study for asymmetric construction of the hydroxyl group at the 2-position of 2-hydroxy-3-nitropropanic acid used as the starting material and also requires the study of the purification process of the resulting product because the stereoselectivity of condensation is about 8:2, which is not so high. The method disclosed in Japanese Patent Laid-open No.309840/1995 is not industrially advantageous because the stereo-selectivity of cyanohydration is about 7:3, which thus requires a technique to purify the objective substance, involving a great loss of isomers during purification. According to the method in Tetrahedron Letters, 35 (33), 6123 (1994), both the yield and stereospecificity are high, but taking account of the fact that the method requires a long time such as 3 days for nitroaldol reaction and 2 days for the hydrolysis of nitro group and also requires the use of complexes of relatively expensive rare earth elements with 1,1'-bi-2-naphthol, the method is not suitable for the production at an industrial scale.

So as to solve these problems, eager investigations have been carried out. Consequently, good results have been obtained according to the present invention. Thus, the present invention is described hereinbelow.

DISCLOSURE OF THE INVENTION

The present invention relates to the following methods (1) through (3).

(1) A method for producing an optically active erythro-3-amino-2-hydroxybutyric ester represented by the formula (III);

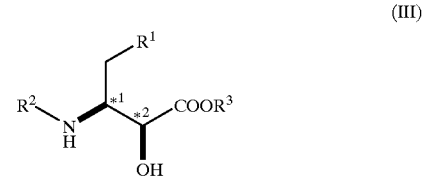

(III)

(wherein $R^1$ represents phenyl group or cyclohexyl group, $R^2$ represents a protective group and $R^3$ represents alcohol residue; the steric configuration of *2 represents S configuration if *1 is of S configuration and represents R configuration if *1 is of R configuration), comprising oxidizing a threo- or threo erythro -3-amino-2-hydroxy-butyric ester, optically active at 3-position, as represented by the following formula (I);

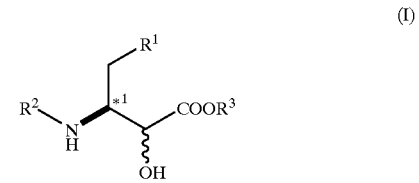

(I)

(wherein $R^1$, $R^2$ and $R^3$ represent the same as described above; and the steric configuration of *1 represents S configuration or R configuration), to produce an optically active 3-amino-2-oxobutyric ester represented by the following formula (II);

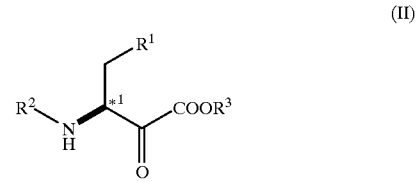

(II)

(wherein $R^1$, $R^2$, $R^3$ and *1 independently represent the same as described above), then reducing erythro-selectively the carbonyl group at the 2-position thereof by using aluminium alkoxide.

(2) A method for producing an optically active (2,3)-erythro-3-amino-2-hydroxybutyric ester of the formula (III), comprising reducing erythro-selectively the carbonyl group at the 2-position of an optically active 3-amino-2-oxobutyric ester by using aluminium alkoxide.

(3) A method for producing an optically active (2,3)-erythro-3-amino- or protected ($R^2$-)amino-2-hydroxybutyric acid, comprising hydrolyzing the optically active (2,3)-erythro-3-amino-2-hydroxybutyric ester of the formula (III) obtained above in (1) or (2).

BEST MODE FOR CARRYING OUT THE INVENTION

The present invention will now be described in detail hereinbelow.

Any known protective group of amino group may be used satisfactorily as the protective group ($R^2$) of amino group in accordance with the present invention, and preferably, the protective group includes lower alkylcarbonyls having 1 to 6 carbon atoms which may be substituted or unsubstituted, such as formyl, acetyl, trifluoroacetyl and pivaloyl, and substituted or unsubstituted benzoyls as acyl-type protective groups; substituted or unsubstituted benzyloxycarbonyls, alkoxycarbonyls with 1 to 6 carbon atoms, and cycloalkanoxycarbonyls as urethane-type protective groups; and other protective groups including (a) substituted or unsubstituted arylsulfonyls or (b) sulfonyls such as substituted or unsubstituted benzene sulfonyls, for example o-nitrobenzene sulfonyl and (c) substituted or unsubstituted phenyl-substituted lower alkyls such as trityl. The substituents in them include halogen atoms, nitro group, hydroxyl group and cyano group and the like.

The $R^3$ forming the ester includes lower alkyls with 1 to 6 carbon atoms which may be substituted or unsubstituted, for example methyl, ethyl, propyl, isopropyl, butyl, isobutyl, tertiary butyl, pentyl, and hexyl; and substituted or unsubstituted aryls, such as substituted phenyls and unsubstituted phenyls. The substituents in them include halogen atoms, nitro group, hydroxyl group and cyano group.

More specifically, compounds represented by the formula (I) include what will be described below
isopropyl (3S)-3-(N-Boc) amino-4-phenyl-2-hydroxybutyate
isopropyl (3S)-3-(N-Z) amino-4-phenyl-2-hydroxybutyrate
isopropyl (3S)-3-N-acetylamino-4-cyclohexyl-2-hydroxybutyrate N-Z represents N-benzyloxycarbonyl; and N-Boc represents N-tert-butoxycarbonyl.

In accordance with the present invention, the method for oxidizing the hydroxyl group in the formula (I) into a compound of the formula (II) is with no specific limitation, as long as secondary alcohol can be oxidized into a carbonyl group according to the method, and the method includes an oxidation method by using chromic acids, an oxidation method with manganese dioxides, an oxidation method with dimethylsulfoxide (abbreviated as DMSO hereinbelow), an oxidation method with nitroxyl compounds and the like. Preferable methods include the following: (a) the oxidation method by using chromic acids includes a method by using complexes of chromic acids with pyridine such as pyridinium chlorochromate and pyridinium dichromate; (b) the oxidation method with dimethylsulfoxide (abbreviated as DMSO hereinbelow) includes a oxidation method using DMSO in the form of an active sulfonium salt, by using electrophilic reagents/DMSO or hydrogen donor.electrophilic reagents/DMSO, such as acetic anhydride/DMSO, triethylamine.sulfur trioxide pyridine complex/DMSO, dicyclohexylcarbodiimide.pyridinium trifluoroacetate/DMSO, and water-soluble carbodiimide hydrochloride salt-.pyridinium trifluoroacetate/DMSO; and (c) the oxidation method with nitroxyl compounds includes a method using 2,2,6,6-tetramethylpiperidine-1-oxyl (abbreviated as TEMPO hereinbelow) or TEMPO generated in a reaction system by using 2,2,6,6-tetramethylpiperidine (abbreviated as TEMP hereinbelow) and oxidants, for example hydrogen peroxide, organic peracids (meta-chloroperbenzoic acid, peracetic acid, perphthalic acid, etc.), or metal oxidants (copper chloride, copper nitrate, ferrocyanate salts, etc.).

Preferably, use is made of the oxidation method with a low toxic reagent DMSO or the oxidation method with nitroxyl compounds among these methods, and more preferably, the method using acetic anhydride/DMSO or the method with TEMPO (abbreviated as TEMPO oxidation hereinbelow) is carried out, which can achieve a high yield and requires relatively simple treatment.

For the treatment with acetic anhydride/DMSO, DMSO is used as the solvent while acetic anhydride is added at 2 to 10 equivalents, preferably 3 to 5 equivalents to a reaction substrate. The reaction temperature is generally 15° C. to a reflux temperature of solvent, preferably room temperature never requiring temperature adjustment.

After termination of the reaction, water addition was effected followed by extraction, washing and drying and subsequent concentration and purification by silica gel chromatography if necessary, to obtain the compound of the formula (II).

For TEMPO oxidation, alternatively, TEMPO for use as the catalyst includes substituted TEMPOs, for example 4-methoxy-TEMPO, 4-hydroxy-TEMPO benzoate and 4-acetoamide-TEMPO, and the amount thereof to be used is at 0.01 to 100 mol % to an alcohol compound as the reaction substrate, and the amount is preferably at 0.05 to 5 mol %, more preferably at about 0.1 to 1 mol % to the reaction substrate, when used together with co-oxidants. The co-oxidants to be used include hypohalogenite or halogenite such as sodium hypochlorite, calcium hypochlorite and sodium bromide, halogens such as chloride, and organic peracids such as meta-chloroperbenzoic acid, and the amount thereof to be used is at 0.5 to 10 equivalents, preferably at about 1 to 5 equivalents. When hypohalogenite salts such as sodium hypochlorite are used, halogeno-ions such as bromide ion, in the form of for example sodium bromide and potassium bromide, are added as an reaction promoter at 5 to 150 mol %, followed by addition of sodium hydrogen carbonate to maintain the pH at weak alkalinity, for example 7 to 10, preferably about 7 to 8 for facilitating the reaction.

The reaction is effected solely in organic solvents when the co-oxidants are dissolved in the organic solvents or in a bi-layer system of water and an organic solvent when the co-oxidants are a water-soluble inorganic salt. Any organic solvent separable at some extent from water and capable of dissolving the compound of the formula (I) is satisfactory, with no specific limitation, including hydrocarbon halides such as methylene chloride and chloroform, aromatic hydrocarbons such as benzene, toluene, and xylene, ethers such as diethyl ether, diisopropyl ether, and tetrahydrofuran, aliphatic hydrocarbons such as pentane, hexane, and heptane, esters such as ethyl acetate, isopropyl acetate and butyl acetate, for single use thereof or for use in a mixture solvent thereof.

The reaction temperature is −15° C. to a temperature suitable for solvent reflux, preferably 0° C. to room temperature with no requirement of temperature adjustment. The reaction is proceeded, by allowing the compound of the formula (I) to be dissolved in a solvent, followed by addition of TEMPO and an additive and gradual addition of a co-oxidant under vigorous stirring. After termination of the reaction, the co-oxidant is decomposed by using iodide ion, for example, sodium iodide and potassium iodide, followed by neutralization, and thereafter, procedures such as layer separation, extraction, washing and drying are carried out. By concentrating the reaction solution after such treatment, followed by purification by silica gel column chromatography if necessary, the compound of the formula (II) can be obtained. The erythro-selective reduction of the resulting carbonyl group in the formula (II) is progressed by hydrogen transfer reaction by using aluminium alkoxide. The aluminium alkoxide to be used is with no specific limitation, and includes for example aluminium isopropoxide, aluminium ethoxide, and aluminium tert-butoxide. The amount thereof to be used is 0.1 to 10 equivalents, preferably 0.5 to 5 equivalents. As the reaction solvent, generally, an alcohol is used because of the involvement thereof in the reaction. For example, lower alcohols with 1 to 6 carbon atoms, such as methanol, ethanol, n-propanol, isopropanol, n-butanol, 2-butanol, and tert-butanol, are included. The reaction temperature is generally room temperature to a reflux temperature of solvent; preferably, the reaction is conducted under the heating from 40° C. to a reflux temperature of solvent to promote the reaction.

Additionally, aluminum alkoxide may be produced in the reaction system, which is then used. A method for producing aluminium alkoxide in the reaction system comprises adding aluminium to an alcohol which is corresponding to the alkoxide, and further adding an activating agent for reaction promotion, and dissolving the agent under heating. The reaction temperature is room temperature to a reflux temperature of solvent, and the reaction temperature is generally a reflux temperature of solvent, so as to promote the reaction. The activating agent includes for example mercury (II) chloride, iodine, and carbon tetrachloride, and any of them may satisfactorily be used. The amount of them for use is at about 0.1 to 10 mol % to the alcohol used. The other conditions are the same as in the reaction by using the aluminium alkoxide. After termination of the reaction, aluminium hydroxide is dissolved in the solution by acidifying the resulting liquid with aqueous hydrochloric acid solution or aqueous sulfuric acid solution, followed by extraction, washing, drying and concentration. By purifying the concentrate by re-crystallization and the like, the compound of the formula (III) in a high purity can be obtained.

Because ester exchange occurs in the ester group $R^3$ in the formula (II) due to the presence of trialkoxyaluminium during reduction, the trialkoxyaluminium to be used in the reaction is preferably $(R^3O)_3Al$, while an alcohol represented by $R^3OH$ is preferably used as the reaction solvent.

Furthermore, the compound of the formula (I) as the starting material is known and can readily be produced by a method utilizing cyanohydration of optically active phenylalanine as a starting material; for example, the compound with $R^1$ being phenyl can be produced by protecting the amino group and carboxyl group of 3-amino-2-hydroxy-4-phenylbutyric acid as described in Journal of Medicinal Chemistry, 20, 510 (1977); the compound with $R^1$ being cyclohexyl can be produced by protecting the amino group and carboxyl group of 3-amino-4-cyclohexyl-2-hydroxybutyric acid as described in Journal of Medicinal Chemistry, 33(10), 2707 (1990).

In accordance with the present invention, the starting material threo- or threo.erythro-3-amino-2-hydroxybutyric ester, optically active at 3-position, as shown in the formula (1) which is readily synthesized from a readily available optically active amino acid, can simply be converted into the objective optically active erythro-3-amino-2-hydroxybutyric ester under relatively mild reaction conditions in a high yield and in a high optical purity. In accordance with the present invention, for example, the butyric esters can be obtained in an optical purity of 90% or more, preferably 95% or more.

Because a higher conversion ratio into the erythro compound is attained as the ratio of the threo compound in the compound represented by the formula (I) as the starting material is higher, the effect of the present invention is enhanced.

The method for introducing the resulting ester compound of the formula (III) into the corresponding carboxylic acid includes hydrolytic reactions by acids and hydrolytic reactions by bases, but because even a protective group of amino group is generally hydrolyzed by the hydrolysis by acids, the hydrolysis by bases is generally in case the protective group of amino group is retained.

For the hydrolysis by acids, the acids to be used include mineral acids such as hydrochloric acid, sulfuric acid and hydrobromic acid, and organic acids such as acetic acid, trifluoroacetic acid, p-toluenesulfonic acid and camphorsulfonic acid, and generally, mineral acids which are relatively inexpensive and easy handleable, such as hydrochloric acid and sulfuric acid are used. The amount thereof to be used is variable, depending on acids to be used, with no specific limitation, but generally, the amount is about 0.1 to 50-fold equivalents, preferably about 1 to 20-fold equivalents to the compound of the formula (III). As the reaction solvent, any non-hydrolyzable solvent can be used, with no specific limitation, but frequently, lower alcohol having about 1 to 4 carbon atoms such as methanol and ethanol, tetrahydrofuran, and dioxane, which mix well with water and promote hydrolysis reaction, are used. Water is added at one equivalent or more to the compound of the formula (III), for facilitating the reaction. The reaction temperature varies, depending on the acids to be used, with no specific limitation, but generally, the temperature is 0° C. to a reflux temperature of solvent, preferably a reflux temperature of solvent because of a rapid reaction rate. After termination of the reaction, the resulting product is treated in a conventional manner, to obtain carboxylic acid.

For the hydrolysis by bases, alternatively, the bases to be used include alkali metal hydroxides such as sodium hydroxide, potassium hydroxide, and lithium hydroxide, and organic amines such as trimethylamine, triethylamine, and pyridine, and strong basic alkali metal hydroxides are preferable because they are relatively cheap and easily handled and reaction rate is rapid, are preferable. The amount thereof to be used is variable, depending on bases to be used, with no specific limitation, but generally, the amount is in about 0.1 to 50-fold equivalents, preferably 1 to 20-fold equivalents to the compound of the formula (III). As the reaction solvent, any non-hydrolyzable solvent is satisfactory, with no specific limitation, but lower alcohols such as methanol and ethanol, tetrahydrofuran and dioxane, which are water-miscible enough to promote the hydrolysis, are frequently used. The reaction is facilitated, by adding one or more equivalents of water to the compound of the formula (III). The reaction temperature is variable, depending on bases to be used, with no specific limitation, but the reaction is generally facilitated in −20° C. to a reflux temperature of solvent, and is carried out at a relatively mild condition of −20° C. to 40° C. in case the protective group of amino group is retained. After termination of the reaction, the resulting product is treated according to a conventional manner, to obtain carboxylic acid.

DESCRIPTION OF THE PREFERRED EMBODIMENTS

The present invention will now be described in more detail with reference to the Examples of the present invention, but the present invention should not be construed as being limited to these Examples.

EXAMPLE 1

(A) Synthesis of isopropyl (3S)-3-(N-tert-butoxycarbonyl)amino-4-phenyl-2-oxobutyrate In 50 ml of toluene was dissolved 5.0 g of isopropyl (2R, 3S)-3-(N-Boc)amino-4-phenyl-2-hydroxybutyrate (herein and hereinafter, N-Boc represents N-tert-butoxycarbonyl), followed by addition of 50 ml of water to the resulting mixture and subsequent addition of 1.52 g of sodium bromide and 4.0 g of sodium hydrogen carbonate, and the resulting mixture was cooled below 10° C. 0.012 g of TEMPO was added to the mixture, followed by gradual dropwise addition of 10.11 g of an aqueous 12% sodium hypochlorite solution under vigorous stirring. After termination of dropwise addition, the resulting mixture was stirred for about one hour, and after the termination of the reaction was confirmed, 0.3 g of potassium iodide was added followed by further addition of 10% potassium hydrogen sulfate to adjust the resulting mixture to pH 7 and subsequent layer separation, and the resulting aqueous layer was extracted in toluene. The extract solution was washed with an aqueous 0.1N sodium thiosulfate solution and then with water, and dried over magnesium sulfate, followed by filtration and concentration under reduced pressure, to quantitatively obtain 5.09 g of isopropyl (3S)-3-(N-Boc)amino-4-phenyl-2-oxobutyrate. The NMR analysis thereof is shown below.

1H-NMR (CDCl$_3$); δ (ppm) 1.34 (d, 6H, J=6.3 Hz); 1.39 (S, 9H); 1.69~1.82 (br, 1H); 2.92~3.28 (m, 2H); 4.98~5.10 (br, 1H); 5.15 (t of d, 1H, J=6.3, 12.6 Hz); 7.09~7.36 (m, 5H).

(B) Synthesis of isopropyl (2S, 3S)-3-(N-Boc)amino-4-phenyl-2-hydroxybutyrate

In 10 ml of isopropanol was dissolved 1.0 g of isopropyl (3S)-3-(N-Boc)amino-4-phenyl-2-oxobutyrate, followed by addition of 0.7 g of aluminium isopropoxide, and heating under reflux for 4 hours. After the termination of the reaction was confirmed, an aqueous 1N hydrochloric acid solution was added to the resulting mixture, to adjust the mixture to pH 3.0, and the resulting mixture was concentrated under reduced pressure. The concentrate was diluted with ethyl acetate and water, followed by layer separation, and the resulting aqueous layer was extracted in ethyl acetate. The extract solution was washed in water and saturated sodium chloride solution, and dried over anhydrous magnesium sulfate, followed by filtration and concentration, to obtain 0.95 g of isopropyl (2S, 3S)-3-(N-Boc)amino-4-phenyl-2-hydroxybutyrate in a yield of 94.5%. The results of the HPLC analysis thereof are shown below. HPLC analysis conditions

| | |
|---|---|
| Column: | Inertsil ODS-2 (GL Science) |
| | 4.6 φ × 250 mm |
| Column temperature: | 35° C. |
| Eluent: | acetonitrile:aqueous 0.02 M ammonium dihydrogen phosphate solution (pH 2.5) = 6:5 |
| Flow rate: | 1.0 ml/min |
| Retention time: | 10.1 minutes for (2S, 3S) compound |
| | 11.9 minutes for (2R, 3S) compound |
| Yield ratio: | (2S, 3S):(2R, 3S) = 93.8:6.2 |

The resulting isopropyl (2S, 3S)-3-(N-Boc)amino-4-phenyl-2-hydroxybutyrate of 0.95 g was subjected to re-crystallization by using n-hexane, to obtain a mixture of isomers at a ratio of (2S, 3S):(2R, 3S)=99.3:0.7 in a yield of 83.2%, of which the NMR analysis is shown below.

1H-NMR (CDCl$_3$); δ (ppm) 1.26 (d of d, 6H, J=6.3, 8.2 Hz); 1.35 (S, 9H); 2.67~2.78 (m, 2H); 3.31 (br, 1H); 4.22~4.38 (m, 2H); 4.82~4.93 (br, 1H); 5.00 (t of d, 1H, J=6.2, 12.5 Hz); 7.14~7.32 (m, 5H).

(C) Synthesis of (2S, 3S)-3-(N-Boc)amino-4-phenyl-2-hydroxybutyric acid

In 10 ml of methanol was dissolved 0.5 g of isopropyl (2S, 3S)-3-(N-Boc)amino-4-phenyl-2-hydroxybutyrate, followed by addition of 1.38 g of aqueous 3N sodium hydroxide solution, and the resulting mixture was washed at room temperature for 2 hours for the promotion of the hydrolysis reaction. After the termination of the reaction was confirmed, aqueous 1N hydrochloric acid solution was added to the resulting mixture to adjust the mixture to pH 3.0, followed by concentration under reduced pressure. The concentrate was diluted with ethyl acetate and water, followed by layer separation, and the resulting ethyl acetate layer was washed with saturated sodium chloride solution. Furthermore, the ethyl acetate layer was dried over anhydrous magnesium sulfate, filtered and concentrated, to obtain (2S, 3S)-3-(N-Boc)amino-4-phenyl-2-hydroxybutyric acid of 0.38 g in a yield of 86.9%. The NMR analysis is shown below.

1H-NMR (DMSO-d6); δ (ppm) 1.26 (S, 9H); 2.62~2.78 (m, 2H); 3.39~3.55 (m, 1H); 3.85~4.06 (m, 2H); 6.67 (br d, 1H); 7.10~7.30 (m, 5H).

EXAMPLE 2

(A) Synthesis of isopropyl (3S)-3-N-acetylamino-4-cyclohexyl-2-oxobutyrate

In 9 ml of dimethylsulfoxide was dissolved 2.0 g of isopropyl (2R, 3S)-3-N-acetylamino-4-cyclohexyl-2-hydroxybutyrate, followed by further addition of 3 ml of acetic anhydride, and the resulting mixture was stirred overnight at room temperature. After the termination of the reaction was confirmed, water was added to the resulting mixture, followed by extraction with ethyl acetate. The extract solution was washed with an aqueous saturated sodium hydrogen carbonate solution and saturated sodium chloride solution, and dried over anhydrous magnesium sulfate. After drying, filtration and concentration under reduced pressure were facilitated, to quantitatively obtain isopropyl (3S)-3-N-acetylamino-4-cyclohexyl-2-oxobutyrate of 2.06 g. The NMR analysis is shown below.

1H-NMR (CDCl$_3$); δ (ppm) 0.78~1.98 (m, 13H); 1.36 (d of d, 6H, J=1.2, 6.3 Hz); 2.04 (s, 3H); 5.11~5.30 (m, 2H); 6.22~6.34 (br, 1H).

(B) Synthesis of isopropyl (3S)-3-N-acetylamino-4-cyclohexyl-2-hydroxybutyrate

In 10 ml of isopropanol was dissolved 1.0 g of isopropyl (3S)-3-N-acetylamino-4-cyclohexyl-2-oxobutyrate, followed by further addition of 0.76 g of aluminium isopropoxide, and the resulting mixture was refluxed under heating for 2 hours. After the termination of the reaction was confirmed, aqueous 1N hydrochloric acid solution was added to the resulting mixture to adjust the mixture to pH 3.0, followed by concentration under reduced pressure. The concentrate was diluted with ethyl acetate and water, followed by layer separation, and the resulting aqueous layer was extracted with ethyl acetate. The extract solution was washed with water and saturated sodium chloride solution and dried over anhydrous magnesium sulfate, followed by filtration and concentration, to obtain isopropyl (2S, 3S)-3-N-acetylamino-4-cyclohexyl-2-hydroxybutyrate of 0.97 g in a yield of 98.0%. The results of the HPLC analysis and NMR analysis thereof are shown below. HPLC analysis conditions

| | |
|---|---|
| Column: | Inertsil ODS-2 (GL Science) |
| | 4.6 φ × 250 mm |
| Column temperature: | 35° C. |
| Eluent: | acetonitrile: aqueous 0.02 M ammonium dihydrogen phosphate solution (pH 2.5) = 4:6 |
| Flow rate: | 1.0 ml/min |
| Retention time: | 11.1 minutes for (2S, 3S) compound |
| | 11.3 minutes for (2R, 3S) compound |
| Yield ratio: | (2S, 3S):(2R, 3S) = 96:4 |

1H-NMR (CDCl$_3$); δ (ppm) 0.62~1.98 (m, 13H); 1.30 (d, 6H, J=6.2 Hz); 2.02 (s, 3H); 3.45 (d, 1H, J=5.3 Hz); 4.29 (d of d, 1H, J=2.9, 5.3 Hz); 4.38~4.53 (m, 1H); 5.13 (t of d, 1H, J=6.3, 12.5 Hz); 5.95 (br, 1H).

(C) Synthesis of (2S, 3S)-3-N-acetylamino-4-cyclohexyl-2-hydroxybutyric acid

In 150 ml of methanol was dissolved 190.1 g of isopropyl (2S, 3S)-3-N-acetylamino-4-cyclohexyl-2-hydroxybutyrate, followed by addition of 100 ml of aqueous 1N sodium hydroxide solution, and the resulting mixture was stirred at room temperature for 2 hours, for the promotion of the hydrolysis reaction. After the termination of the reaction was confirmed, aqueous 1N hydrochloric acid solution was added to the resulting mixture to adjust the mixture to pH 3.0, followed by concentration under reduced pressure. The concentrate was diluted with ethyl acetate and water, followed by layer separation, and the resulting ethyl acetate layer was washed with saturated sodium chloride solution. Furthermore, the ethyl acetate layer was dried over anhydrous magnesium sulfate, filtered and concentrated, to obtain (2S, 3S)-3-N-acetylamino-4-cyclohexyl-2-hydroxybutyric acid of 154.0 g in a yield of 95.0%. The NMR analysis is shown below.

1H-NMR (DMSO-d6); δ (ppm) 0.68~1.78 (m, 13H); 1.77 (s, 3H); 3.40~3.51 (m, 1H); 3.86 (d, 1H, J=2.8 Hz); 4.10~4.26 (m, 1H); 7.43 (br d, 1H).

Industrial Applicability

In accordance with the present invention, erythro-3-amino-2-hydroxybutyric esters or erythro-3-amino-2-hydroxybutyric acid at a purity of 90% or more, preferably 95% or more can readily be obtained in good yields, by reducing erythro-selectively optically active threo- or threo erythro-3-amino-2-oxobutyric ester, which ester can readily be synthesized from a readily available optically active amino acid. These erythro compounds are the important intermediates of pharmaceutical agents, for example HIV protease inhibitor, and therefore, the present invention is applicable industrially as a method for producing the intermediates.

What is claimed is:

1. A method for producing an optically active (2,3)-erythro-3-amino-2-hydroxybutyric ester represented by the following formula (III):

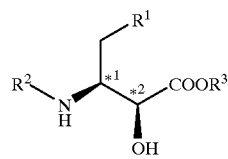

(III)

(wherein R$^1$ represents phenyl group or cyclohexyl group; R$^2$ represents a protective group and R$^3$ represents an unsubstituted or substituted alkyl residue; the steric configuration of *2 represents S configuration if *1 is of S configuration and represents R configuration if *1 is of R configuration), comprising oxidizing a threo- or threo-erythro-3-amino-2-hydroxybutyric ester, optically active at 3-position, as represented by the following formula (I):

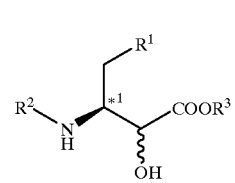

(I)

(wherein R$^1$, R$^2$ and R$^3$ independently represent the same as described above; and the steric configuration of *1 represents S configuration or R configuration), to produce an optically active 3-amino-2-oxobutyric ester represented by the following formula (II):

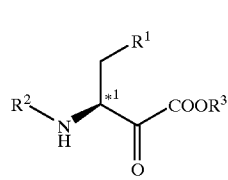

(II)

(wherein R$^1$, R$^2$, R$^3$ and *1 independently represent the same as described above), and reducing erythro-selectively the carbonyl group at the 2-position thereof by using aluminum alkoxide.

2. A method for producing an optically active (2,3)-erythro-3-amino-2-hydroxybutyric ester of the formula (III), comprising reducing erythro-selectively the carbonyl group at the 2-position of an optically active 3-amino-2-oxobutyric ester by using aluminium alkoxide.

3. A method for producing an optically active (2,3)-erythro-3-amino-2-hydroxybutyric acid represented by the following formula:

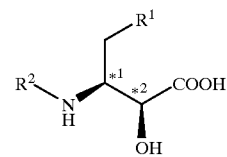

(wherein R$^1$ represents a phenyl group or a cyclohexyl group and R$^2$ represents a protective group; the steric configuration of *2 represents S configuration if *1 is of S configuration and represents R configuration if *1 is of R configuration), comprising oxidizing a threo- or threo erythro-3-amino-2-hydroxybutyric ester, optically active at the 3-position, as represented by the following formula (I):

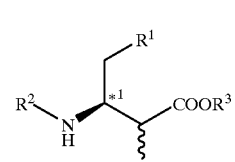

(I)

(wherein R$^1$ and R$^2$ independently represent the same as described above, and R$^3$ represents an unsubstituted or substituted alkyl residue; and the steric configuration of *1 represents S configuration or R configuration), to produce an optically active 3-amino-2-oxobutyric ester represented by the following formula (II):

(II)

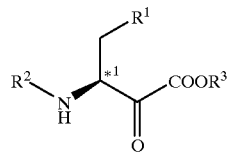

(wherein $R^1$, $R^2$, $R^3$ and *1 independently represent the same as described above), and reducing erythro-selectively the carbonyl group at the 2-position thereof by using aluminum alkoxide to produce an optically active (2,3)-erythro-3-amino-2-hydroxybutyric ester represented by the following formula (III):

(III)

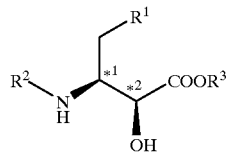

(wherein $R^1$, $R^2$ and $R^3$ independently represent the same as described above; the steric configuration of *2 represents S configuration if *1 is of S configuration and represents R configuration if *1 is of R configuration), and further hydrolyzing hydroxybutyric ester.

4. A method for producing an optically active (2,3)-erythro-3-amino-2-hydroxybutyric acid represented by the following formula:

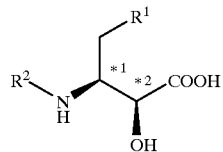

(wherein $R^1$ represents a phenyl group or a cyclohexyl group and $R^2$ represents a protective group; the steric configuration of *2 represents S configuration if *1 is of S configuration and represents R configuration if *1 is of R configuration), comprising reducing erythro selectively the carbonyl group at the 2-position in an optically active 3-amino-2-oxobutyric ester represented by the following formula (II):

(II)

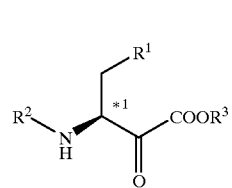

(wherein $R^1$ and $R^2$ independently represent the same as described above and $R^3$ represents an unsubstituted or substituted alkyl residue; and the steric configuration of *1 represents S configuration or R configuration) by using aluminum alkoxide to produce an optically active (2,3)-erythro-3-amino-2-hydroxybutyric ester represented by the following formula (III):

(III)

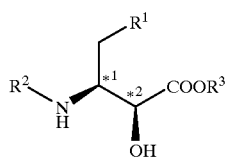

(wherein $R^1$ and $R^2$ independently represent the same as described above, and $R^3$ represents an unsubstituted or substituted alkyl residue; the steric configuration of *2 represents S configuration if *1 is of S configuration and represents R configuration if *1 is of R configuration), and further hydrolyzing said hydroxybutyric ester.

* * * * *